United States Patent
Andrich et al.

(10) Patent No.: US 11,931,596 B2
(45) Date of Patent: Mar. 19, 2024

(54) PHOTOTHERAPY DEVICE

(71) Applicant: Lumitex, Inc., Strongsville, OH (US)

(72) Inventors: Brian Andrich, Medina, OH (US);
Peter W. Broer, Bratenahl, OH (US);
Michael Kerns, Copley, OH (US);
David G. Felty, Parma, OH (US)

(73) Assignee: Lumitex, Inc., Strongsville, OH (US)

( * ) Notice: Subject to any disclaimer, the term of this patent is extended or adjusted under 35 U.S.C. 154(b) by 38 days.

(21) Appl. No.: 17/761,060

(22) PCT Filed: Sep. 21, 2020

(86) PCT No.: PCT/US2020/051723
§ 371 (c)(1),
(2) Date: Mar. 16, 2022

(87) PCT Pub. No.: WO2021/061540
PCT Pub. Date: Apr. 1, 2021

(65) Prior Publication Data
US 2022/0339466 A1    Oct. 27, 2022

Related U.S. Application Data

(60) Provisional application No. 62/903,959, filed on Sep. 23, 2019.

(51) Int. Cl.
*A61N 5/06* (2006.01)

(52) U.S. Cl.
CPC ............. *A61N 5/0621* (2013.01); *A61N 5/06* (2013.01); *A61N 2005/0652* (2013.01)

(58) Field of Classification Search
CPC . A61B 5/0621; A61N 5/06; A61N 2005/0652
See application file for complete search history.

(56) References Cited

U.S. PATENT DOCUMENTS

| | | |
|---|---|---|
| 6,596,016 B1 | 7/2003 | Vreman et al. |
| 2007/0208397 A1 | 9/2007 | Gardner |
| 2009/0018622 A1 | 1/2009 | Asvadi et al. |

FOREIGN PATENT DOCUMENTS

| | | |
|---|---|---|
| EP | 3474949 | 5/2020 |
| WO | 2006/101735 | 9/2006 |

OTHER PUBLICATIONS

International Preliminary Report on Patentability for corresponding PCT application PCT/US2020/051723 dated Mar. 15, 2022.

*Primary Examiner* — Shirley X Jian
(74) *Attorney, Agent, or Firm* — Renner, Otto, Boisselle & Sklar, LLP

(57) ABSTRACT

A phototherapy device including a flexible light emitting pad is provided. The phototherapy device allows an infant to be swaddled while the infant simultaneously receives phototherapy treatment on his/her front, back, and sides without the use of external light sources.

23 Claims, 5 Drawing Sheets

PHOTOTHERAPY DEVICE

RELATED APPLICATIONS

This application claims the benefit of U.S. 62/903,959 filed on Sep. 23, 2019; and PCT/US2020/051723 filed on Sep. 21, 2070. Which are both herein incorporated by reference in their entirety.

TECHNICAL FIELD

The present disclosure relates generally to a phototherapy device and system for delivering light to an infant's torso.

BACKGROUND

Phototherapy has long been used to treat newborn infants for various maladies including jaundice. Jaundice is caused by a buildup of bilirubin in the blood of infants. Exposing the infant's skin to certain types of light will quickly reduce the bilirubin to a safe level.

A common problem in the treatment of jaundice, especially in full-term babies, is the inability to swaddle or nurse the baby during treatment. Because treating jaundice typically involves exposing a baby's skin to overhead lights (the light converting bilirubin to another molecule that kidneys typically can filter), the baby's trunk is exposed and unwrapped. Often when a baby is not tucked or swaddled, the baby panics, flails arms, and cries. This often causes a parent or nurse to end treatment prematurely, at the risk of jaundice levels remaining elevated.

Blanket phototherapy for infants with jaundice is widely used in the developed world, with the advantage that it allows infant swaddling and mother/baby bonding during treatment. However, for reasons of economy, it is not widely available in the developing world.

SUMMARY

In a full-term nursery (e.g., a well baby non-NICU), it would be preferable to wrap babies fully in light while at the same time restraining movement of the baby's arms, making babies more comfortable in the normal fetal or wrapped position (also called swaddled). By maintaining a position of light sources relative to the baby, it is also possible to prevent the need for babies to wear protective eye patches.

Conversely, in a premature birth nursery, it may be preferable to not wrap the babies, but to instead direct light to the back of the baby.

It is possible to swaddle a baby during phototherapy by using a flexible light emitting pad and a garment to maintain the position of the flexible light emitting pad relative to the baby. In this way, it is possible to perform phototherapy while at the same time swaddling the infant by providing light using light sources integrated into the flexible light emitting pad that are capable of providing enough light to expose the full (or near full) circumference of a baby's torso at an adequate dosage for effective treatment.

Alternatively, a baby (e.g., a premature baby) may be positioned on top of the flexible light emitting pad without using the garment to wrap the flexible light emitting pad around the baby. In this embodiment, the flexible light emitting pad may be placed on top of a base and the baby may be placed on top of the light emitting pad. The base may be shaped to maintain a position of the baby. For example, the base may include a recessed portion surrounded by raised portions, such that the position of the baby is maintained by the raised portions when the baby is laid down in the recessed portion.

By using a flexible light emitting pad including integrated light sources, it is possible to achieve full 360-degree coverage of an infant's body without requiring overhead lamps or an external light source.

The present disclosure provides a phototherapy device including a flexible light emitting pad(s). The phototherapy device allows an infant to be swaddled while the infant simultaneously receives phototherapy treatment on his/her front, back, and sides without the use of external light sources.

According to one aspect, there is provided a phototherapy device for delivering light to an infant. The device includes a flexible light emitting pad made of a flexible support material and including light sources physically connected to the flexible support material and configured to emit electromagnetic radiation.

Alternatively or additionally, the flexible support material is a gel and the light sources are encased in the gel.

Alternatively or additionally, the light sources include at least one of light emitting diodes (LEDs), micro-LEDs, or organic LEDs (OLEDs).

Alternatively or additionally, the flexible light emitting pad additionally includes a light guide and the light emitted by the light sources is received, propagated, and emitted by the light guide.

Alternatively or additionally, the flexible light emitting pad includes a light emitting surface and a back surface opposite the light emitting surface. The light emitting surface includes surface texturing including depressions and/or protrusions configured to improve air flow to a skin of the infant.

Alternatively or additionally, the flexible light emitting pad includes articulation structures configured to allow the flexible light emitting pad to be wrapped around the infant.

Alternatively or additionally, the articulation structures includes reliefs in the flexible light emitting pad.

Alternatively or additionally, the flexible support material is a cloth material and the light sources and electrical connections to the light sources are printed onto the cloth material.

Alternatively or additionally, the cloth material, light sources, and electrical connections are incased in a gel.

Alternatively or additionally, the cloth material comprises a portion of the garment, such that the light sources and the electrical connects are printed onto the garment.

Alternatively or additionally, the flexible light emitting pad includes a light emitting surface and a back surface opposite the light emitting surface and the flexible light emitting pad includes at least one of a padding or surface texturing. The padding is positioned such that the light emitting surface is located between the light sources and the padding. The surface texturing is included in the light emitting surface. The surface texturing is configured to direct light emitted by the light emitting surface such that the light emitted by the light emitting surface has a specific light output distribution.

Alternatively or additionally, the device additional includes a garment. The garment is configured to receive the infant and the flexible light emitting pad and maintain the position of the flexible light emitting pad relative to the infant.

Alternatively or additionally, the garment includes an inner surface configured to be located adjacent the infant when the infant and the flexible light emitting pad are positioned within the garment and an outer surface opposite the front surface. The outer surface is opaque to light emitted by the light sources and/or includes a reflector configured to reflect light emitted by the light sources towards the inner surface.

Alternatively or additionally, the garment includes a receiving location configured to receive the flexible light emitting pad and to maintain a position of the flexible light emitting pad relative to the infant.

Alternatively or additionally, the receiving location is at least one of an inner surface of the flexible light emitting pad or a pocket.

Alternatively or additionally, the receiving location is a pocket and the pocket includes: an outer wall and an inner wall located opposite the outer wall; the inner wall is positioned between the infant and the flexible light emitting pad when the flexible light emitting pad is received by the pocket and the infant is received by the garment; and the inner wall is at least partially transparent to light emitted by the light sources.

Alternatively or additionally, the garment includes a sack having a closed bottom edge and a partially closed top including a hole through which a neck of the infant extends when the infant is received in the garment. The sack also has two partially closed sides including arm holes through which arms of the infant extend when the infant is received in the garment.

Alternatively or additionally, the garment comprises a wrap configured to be wrapped around and swaddle the infant, such that movement of arms of the infant is restricted. The wrap includes a top surface located opposite a bottom surface. The bottom surface of the wrap faces towards the infant when the infant is received in the garment and when the infant is swaddled by the wrap. The bottom surface has a first fastener. The top surface has a second fastener configured to releasably engage with the first fastener.

Alternatively or additionally, when both the infant and the flexible light emitting pad are received by the garment, light emitted by the light sources illuminates a torso of the infant.

Alternatively or additionally, the device additionally includes circuitry configured to control properties of light emitted by the light sources.

Alternatively or additionally, the circuitry is further configured to modulate the amount of light delivered to the infant via the light sources.

Alternatively or additionally, the circuitry is configured to modulate the amount of light to provide a therapeutically effective dose to treat jaundice in the infant.

Alternatively or additionally, the device further includes a sensor configured to sense at least one of biometric data of the infant or a property of the light emitted by the light sources. The circuitry is configured to receive an output of the sensor and to control the properties of light emitted by the light sources based on the output of the sensor.

Alternatively or additionally, the circuitry is configured to measure a bilirubin level based on the output of the sensor.

Alternatively or additionally, the sensor is configured to sense at least one an amount of light received by the infant or a temperature of the infant. The circuitry is configured to at least one of: reduce an output power of the light sources when the sensed amount of light exceeds a dosage threshold or when the temperature exceeds a temperature threshold; or increase the output power of the light sources when the sensed amount of light is below the dosage threshold and when the temperature is below the temperature threshold.

Alternatively or additionally, the sensor is configured to sense a temperature of the infant. The electromagnetic radiation emitted by the light sources includes infrared light. The circuitry is configured to increase an output of infrared light by the light sources when the sensed temperature of the infant is below a temperature threshold.

Alternatively or additionally, the circuitry includes: a tracking sensor configured to identify a location of the phototherapy device; and a communication interface configured to send the location identified by the tracking sensor.

Alternatively or additionally, the device also includes a power source configured to provide electrical power to the light sources.

Alternatively or additionally, the device includes a reflective surface. The flexible light emitting pad includes a light emitting surface and a back surface opposite the light emitting surface. The reflective surface is positioned adjacent to the back surface, such that the reflective surface directs light emitted from the back surface towards the light emitting surface.

Alternatively or additionally, the flexible light emitting pad and/or the garment comprises a breathable material having a moisture vapor transmission rate ("MVTR") of at least 500 $g/m^2/24$ hrs.

According to another aspect, there is provided a phototherapy device for delivering light to an infant. The device includes a flexible light emitting pad made of a flexible support material and including wavelength converting nanoparticles sources configured to alter a wavelength of incident light.

Alternatively or additionally, the device also includes a garment configured to: receive the infant and the flexible pad and maintain the position of the flexible pad relative to the infant.

Alternatively or additionally, the wavelength converting nanoparticles include quantum dots.

Alternatively or additionally, the wavelength converting nanoparticles include at least one of: upconverting nanoparticles configured to increase a wavelength of the incident light having a wavelength within an upconverting wavelength range; or downconverting nanoparticles configured to decrease a wavelength of the incident light having a wavelength within a downconverting wavelength range.

Alternatively or additionally, the incident light is solar light

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

DETAILED DESCRIPTION

Jaundice is caused in most neonates and a certain percentage of full-term babies when the liver is inadequately developed to filter Bilirubin from the blood. Neonates and full-term babies with jaundice are commonly treated with blue light, which conjugates bilirubin molecules into lumirubin and photobilirubin, isomers of bilirubin which can be filtered by the kidneys.

In cost-sensitive environments typical in developing countries, babies are generally treated with overhead lights. A widely-acknowledged problem with this treatment mode is that the baby is typically left alone on its back with skin exposed under the lights. Commonly, its arms flail and panic often sets in, leaving the baby crying. When this happens, caregivers often disrupt or discontinue treatment to pick up and calm the baby.

Blanket phototherapy provides a desirable alternative, because it allows treatment to take place simultaneously with holding or swaddling the baby, leaving the baby calm as treatment continues without interruption. However, most effective blanket phototherapy tends to be expensive, limiting it to high-end hospitals in the developing world. Fiber optic construction used in the blanket phototherapy generally requires light from a high-power light-source in a remote box with complex electronics, a fan, and an intermediate fiber optic cable to keep heat away from babies, all-together making it too expensive a construction to deliver in cost-sensitive environments.

Lower-cost blanket phototherapy available today typically consists of a simple construction of individual, selectively-terminated fibers—an ineffective pad construction. This construction generally produces spots or points of light, which typically record readings less than the American Association of Pediatrics standard of 27 micro-watts per nanometer per centimeter squared, generally acknowledged globally to be the effective lower limit for infant phototherapy. Also, the system's optical inefficiency requires a high-powered light source with sophisticated electronics and a cooling fan to dissipate the heat generated by the high power LED.

Figure 1:
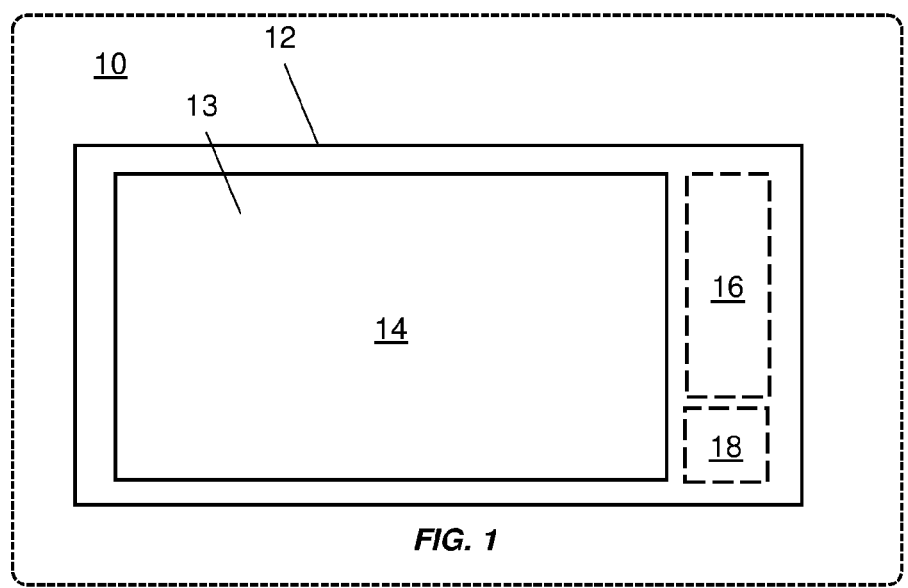
FIG. 1 is a schematic diagram of an exemplary embodiment of a phototherapy system showing flexible light emitting pad.
Figure 2:
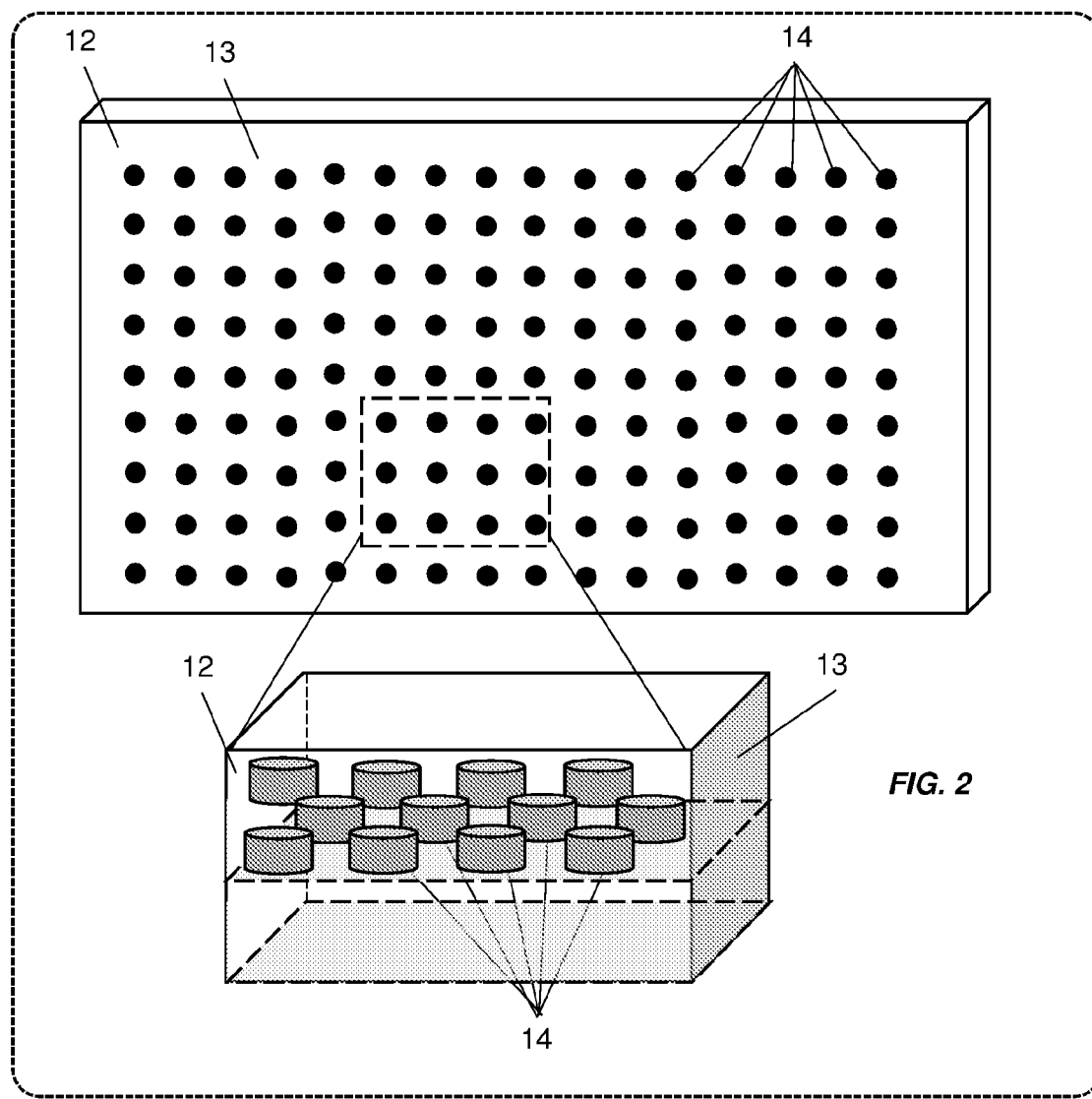
FIG. 2 is a schematic diagram of the flexible light emitting pad of the phototherapy system of FIG. 1 including a zoomed in portion of the flexible light emitting pad.

Turning to FIGS. 1 and 2, a preferred embodiment of the current invention consists of a phototherapy device 10 including a flexible light emitting pad 12. The flexible light emitting pad 12 includes a flexible support material 13 and integrated light sources 14 physically connected to the flexible support material 13. For example, instead of using a separate light source located in a light box, the light sources 14 are integrated into the flexible light emitting pad 12 itself as shown in the zoomed in portion of FIG. 2.

The phototherapy device 10 may additionally include a power source 16 and/or circuitry 18. The power source 16 (e.g., a battery or a plug configured to receive power from an external power source) may be integrated into or attached to the flexible light emitting pad 12.

The circuitry 18 is electrically connected to the light sources 14 and is configured to control properties of light emitted by the light sources 14. The circuitry 18 may modulate the amount of light delivered to the infant via the light sources 14. For example, the circuitry 18 may control at least one of a duration, pattern, wavelength, or intensity of light emitted by the light sources 14 or portion of light sources 14. The circuitry 18 may modulate the amount of light to provide a therapeutically effective dose to treat jaundice in the infant.

The circuitry 18 may have various implementations. For example, the circuitry 18 may include any suitable device, such as a processor (e.g., CPU), programmable circuit, integrated circuit, memory and I/O circuits, an application specific integrated circuit, microcontroller, complex programmable logic device, other programmable circuits, or the like. The circuitry 18 may also include a non-transitory computer readable medium, such as random access memory (RAM), a read-only memory (ROM), an erasable programmable read-only memory (EPROM or Flash memory), or any other suitable medium.

In the embodiment shown in FIG. 2, the flexible light emitting pad 12 is formed from a gel with light sources 14 embedded in the gel. That is, the flexible support material 13 is a gel and the light sources 14 are encased in the gel. As is described in further detail below, the light sources 14 may be mounted to a substrate that is encased in the gel. The light sources 14 may comprise light emitting diodes (LEDs), micro-LEDs, organic LEDs (OLEDs), or any suitable source of light. For example, a clad flat fiber and LEDs may be encased in a gel (e.g., polyurethane). Electrical connection may be made to the LEDs at an edge of the gel. In an alternative embodiment, micro-LEDs (without a separate light guide) may be embedded in the gel. Similarly, electrical connection to provide power to the micro-LEDs may be made at a surface of the light emitting pad.

The gel may be a hydrogel that is at least partially transparent to the light emitted by the light sources 14. The hydrogel may be configured to be biocompatible, such that the hydrogel may be make direct contact with an infant's skin for a duration of time (e.g., multiple hours) without damaging the skin. The flexible light emitting pad 12 may be formed from any gel such as polyurethane or any suitable material capable of wrapping around an infant.

Figure 3:
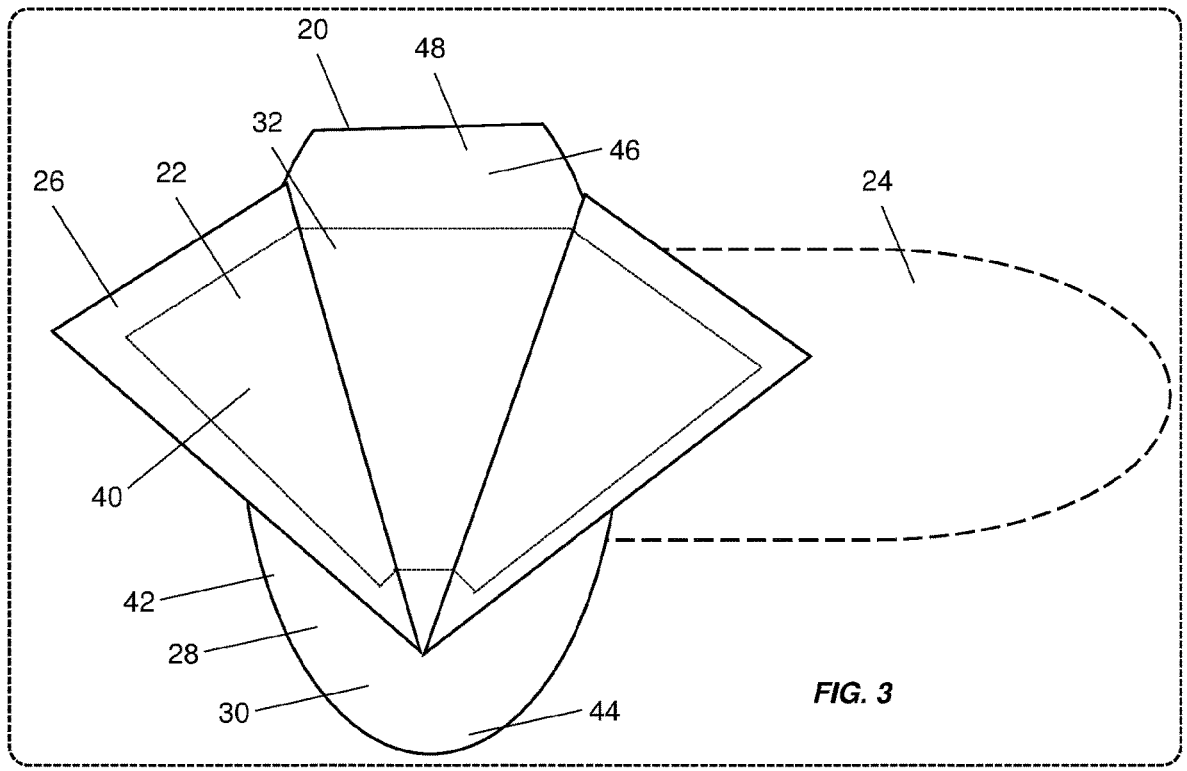
FIG. 3 is a schematic diagram of a garment for maintaining a position of the phototherapy system of FIG. 1 relative to an infant.
Figure 4:
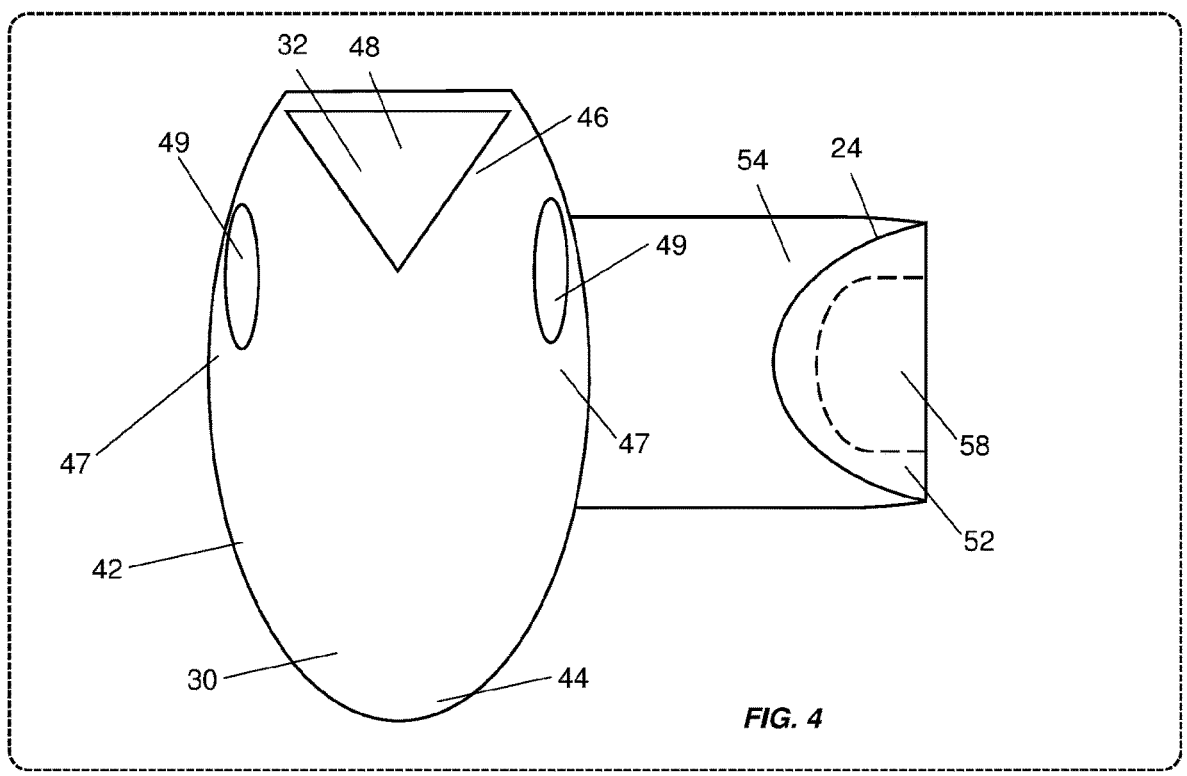
FIGS. 4 and 5 are schematic diagrams of the garment of FIG. 3 with the front surface closed.
Figure 5:
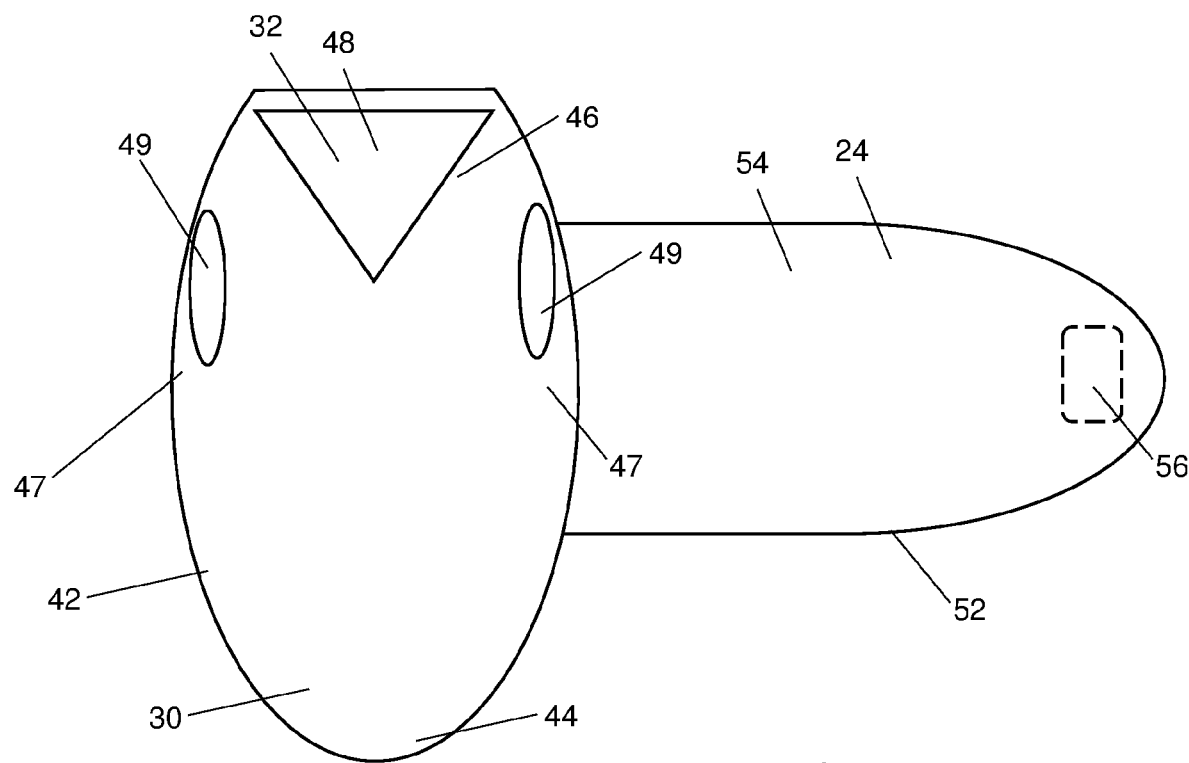

In the embodiment shown in FIGS. 3-5, the phototherapy device 10 additionally includes a garment 20. In FIG. 3, the garment 20 is shown with the front opened, while in FIGS. 4 and 5 the garment is shown with the front closed. The garment 20 is configured both to receive the infant and the flexible light emitting pad 12 and to maintain the position of the flexible light emitting pad 12 relative to the infant (e.g., so that the infant receives phototherapy over the front, back, and sides of their torso simultaneously). The garment 20 includes an inner surface 26 and an outer surface 28 opposite the front surface 26. The inner surface 26 of the garment 20 is configured to be located adjacent the infant (e.g., a chest of the infant) when the infant is received in the garment 20 or adjacent the flexible light emitting pad 12 when located in the garment 20. In this way, when an infant and the flexible light emitting pad 12 are received by the garment 20, light emitted by the light sources 14 illuminates a torso of the infant.

To reduce the amount of light emitted by the light sources 14 that escapes from the garment 20 in a direction away from the infant, the outer surface 28 of the garment 20 or the flexible light emitting pad 12 may be at least partially opaque and or reflective (e.g., to direct light back towards the baby) to light emitted by the light sources 14. For example, the garment 20 may be at least 50%, 70%, 85%, or 90% opaque to light having a wavelength of 430-520 nm.

The garment 20 may include a location(s) 22 for receiving the flexible light emitting pad(s) 12 and for maintaining a position of the flexible light emitting pad 12 relative to the infant. For example, the receiving location 22 may be a pocket shaped to receive the flexible light emitting pad 12. The pocket may include an outer wall 40 and an inner wall 42 located opposite the outer wall 40. The inner wall 42 is positioned between the infant and the flexible light emitting pad 12 when the flexible light emitting pad 12 is received by the pocket and the infant is received by the garment. The inner wall 42 (i.e., the layer of material forming the pocket and located between the flexible light emitting pad 12 and the infant) may be made of a material that minimally absorbs the light emitted by the flexible light emitting pad 12 (i.e., the inner wall 42 is at least partially transparent to light emitted by the light sources 14). For example, the layer of material may be formed of a spun fiber. The pocket may also include a fastening mechanism to maintain the position of the flexible light emitting pad 12 received in the pocket.

Alternatively, the location 22 of the garment 20 may comprise a surface that the flexible light emitting pad 12 is placed onto prior to placing an infant in the garment 20. That is, the flexible light emitting pad 12 may be laid on an internal surface 26 of the garment 20, such that the flexible light emitting pad 12 touches the infant when the infant is placed within the garment 20.

As shown, the garment 20 may include a sack 30 having a closed bottom edge 44, a partially closed top 46, and two partially closed sides 47. The partially closed top 46 includes a hole 48 through which a neck of the infant extends when the infant is received in the garment 20. Similarly, the two partially closed sides 47 include arm holes 49 through which arms of the infant extend when the infant is received in the garment 20.

The sack 30 may further include a front surface and a back surface. The front surface may include an opening 32 and a closure mechanism configured to close the opening 32 of the front surface. The opening 32 may be used to place the infant into the sack 30. The closure mechanism may take the form of any suitable structure for keeping the opening 32 closed. For example, the closure mechanism may comprise one or more of snaps, buckles, Velcro, clips, adhesive strips, a zipper, and/or ties.

The garment 20 may additionally include a wrap 24 configured to be wrapped around and swaddle the infant. The wrap 24 includes a top surface 52 located opposite a bottom surface 54. The bottom surface 54 of the wrap faces towards the infant when the infant is received in the garment 20 and when the infant is swaddled by the wrap 24. The bottom surface 54 has a first fastener 56 and the top surface 52 has a second fastener 58 configured to releasably engage with the first fastener. As will be understood by one of ordinary skill in the art, the first and second fasteners may take the form of any suitable structure for maintaining the position of the wrap 24. For example, the first and second fasteners may comprise one or more of snaps, buckles, Velcro, clips, adhesive strips, a zipper, and/or ties.

The wrap 24 may be releasably attach to the sack 30 via a third fastener. The third fastener may take the form of any suitable structure for securing the wrap 24 to the sack 30. For example, the third fastener may comprise one or more of snaps, buckles, Velcro, clips, adhesive strips, a zipper, and/or ties.

The wrap 24 may be contoured such that, when the infant is swaddled by the wrap 24, an edge of the wrap 24 nearest to and directly below a chin of the infant dips away from the chin of the infant. The contour of the wrap 24 and the arm holes prevent the wrap 24 and the sack 30 from covering a mouth of the infant when the infant is received in the garment 20 and the infant is swaddled by the wrap 24. The contour of the wrap 24 may take any suitable form that dips away from the chin of the infant.

To reduce the amount of light emitted by the light sources 14 that escapes from the garment 20 in a direction away from the infant, the wrap 24 may be at least partially opaque and/or reflective to light emitted by the light sources 14 received by the pocket. For example, the wrap 24 may be at least 50%, 70%, 85%, or 90% opaque to light having a wavelength of 430 nm-520 nm.

The garment 20 may be made from any suitable material. For example, the garment 20 may be made from a blend of cotton, nylon, or other suitable polymers. As an example, the garment 20 may be made from any breathable material that is air permeable.

As an example, the garment 20 may be made from two or more layers of a woven fabric, or if disposable, two or more layers of a spun woven paper-like material. The portion of the garment 20 that contacts an infant's skin when the infant is received in the garment 20 may be made out of a soft fabric-like material that is relatively light transmissive. For example, the garment 20 may be made from a first fabric layer (configured to contact an infant's skin) that is relatively thin and/or loosely woven or the fabric fibers themselves can be relatively transparent or translucent to permit light to pass therethrough. A second fabric layer located opposite the first fabric layer may be quilted to provide added softness. Further, a fill material may be located between the first and second fabric layer and act as insulation to help the infant retain warmth. As another example, the first fabric layer (configured to contact the infant's skin and be located between the infant's skin and the light guide 14) may be quilted to provide added softness.

Figure 6:
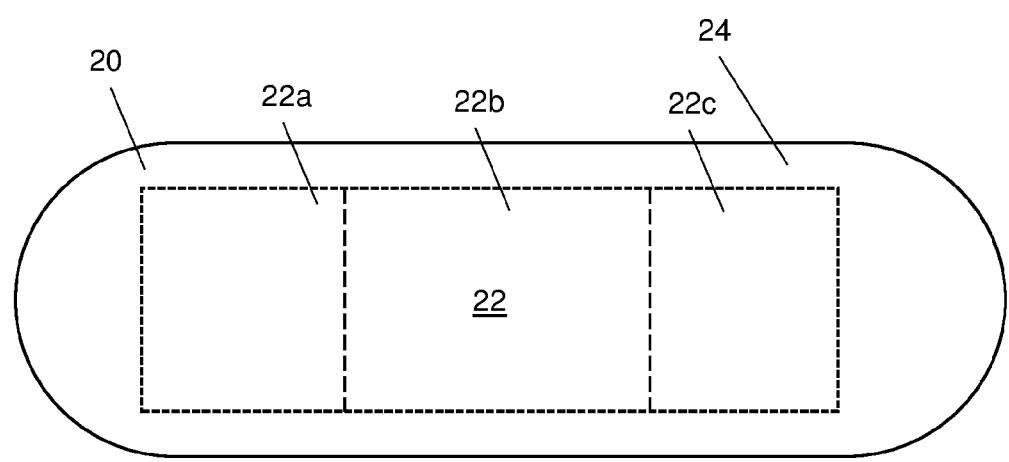
FIG. 6 is a schematic diagram of another embodiment of a garment for maintaining a position of the phototherapy system of FIG. 1 relative to an infant.

Turning to FIG. 6, the garment 20 may not include a sack 30, but may instead be comprised of a wrap 24. That is, the position of the flexible light emitting pad 12 relative to the infant may be maintained by the wrap 24 by itself, without the use of a sack 30.

As shown in FIG. 6, the garment 20 may include multiple locations 22a-c for receiving the flexible light emitting pad 12, e.g., when the phototherapy device 10 includes multiple flexible light emitting pads 12.

In an embodiment, the flexible light emitting pad 12 and/or the garment 20 may be disposable. That is, the flexible light emitting pad 12 and/or the garment 20 may be used by a single patient and subsequently be disposed of.

The flexible light emitting pad 12 and/or the garment 20 may comprise a breathable material. A breathable material may have a moisture vapor transmission rate ("MVTR") of at least 500 g/m$^2$/24 hrs, preferably above 1,000 g/m$^2$/24 hrs, and more preferably above 2,000 g/m$^2$/24 hrs. MVTR indicates the degree of breathability of a film, the higher the MVTR, the higher the degree of breathability. For example, the flexible light emitting pad 12 and/or garment 20 may be made from a material including through holes to improve breathability of the flexible light emitting pad 12. Alternatively, the flexible light emitting pad 12 and/or garment 20 may be made from a woven material.

The light sources 14 may be positioned across the flexible light emitting pad 12 such that the light sources 14 illuminate a front and a back of the infant when wrapped around the infant. The light sources 14 may have a specific pattern on the flexible light emitting pad 12 such that particular areas of an infant are preferentially illuminated.

Figure 7:
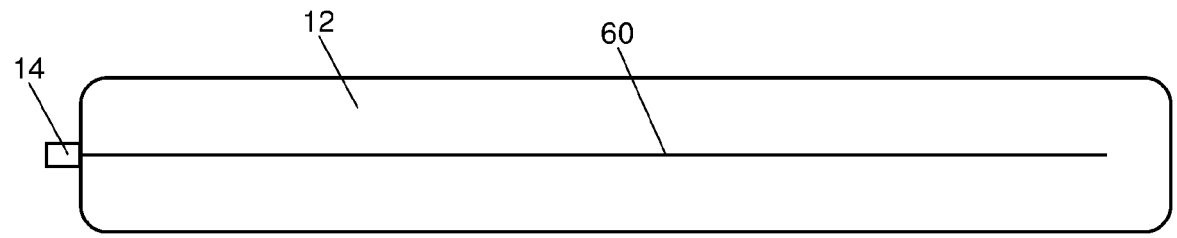
FIG. 7 is a side view of an embodiment of the flexible light emitting pad.
Figure 8:
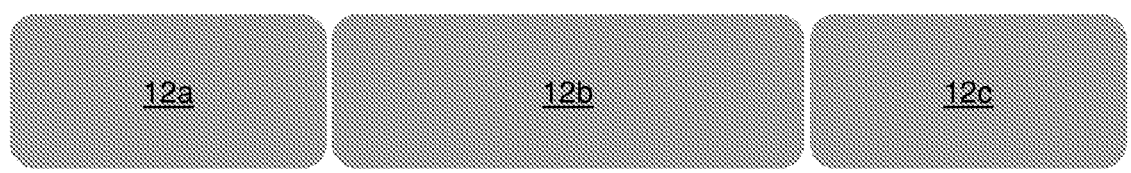
FIG. 8 is a side view of another embodiment of the flexible light emitting pad comprising three physically separate pads.

In the embodiment shown in FIG. 7, the flexible light emitting pad 12 additionally includes a light guide 60. In this embodiment, the light emitted by the light sources 14 is received, propagated, and emitted by the light guide 60. For example, the light guide 60 could take the form of a flat fiber insert and the light source 14 could be arranged in a strip that is aligned along one edge of the insert. With a series of small light sources 14 (e.g., LEDs), light may be well distributed and a rudimentary style of coupling optic may be used (e.g., a molded acrylic strip with a series of indents on one side to receive the LEDs and on the other side a cavity to receive the fiber ends). The fiber ends could be clear UV-cure epoxied in place to make a uniform light coupling.

In another embodiment, the light sources 14 may be located separate from the flexible light emitting pad 12 and light emitted by the light sources 14 may be transmitted to the flexible light emitting pad 12 via light guides. The light guides may be configured such that light is emitted through the light emitting surface 62 via the light guides.

In FIG. 7, the phototherapy device 10 includes a single flexible light emitting pad 12. However, as shown in FIG. 6, the phototherapy device 10 may include multiple flexible light emitting pads 12a-c.

In FIG. 7, the light emitting pad 12 includes a light emitting surface 62 and a back surface 64 opposite the light emitting surface 62. The light emitting surface 62 includes surface texturing 72 (also referred to as contouring) including depressions and/or protrusions to improve comfort to the infant and to improve air flow to skin of an infant that is wrapped within the flexible light emitting pad 12. As will be understood by one of ordinary skill in the art, the surface texturing 72 may include any structures that improve air flow to skin of an infant laid on and/or surrounded by the flexible light emitting pad 12.

Figure 9:
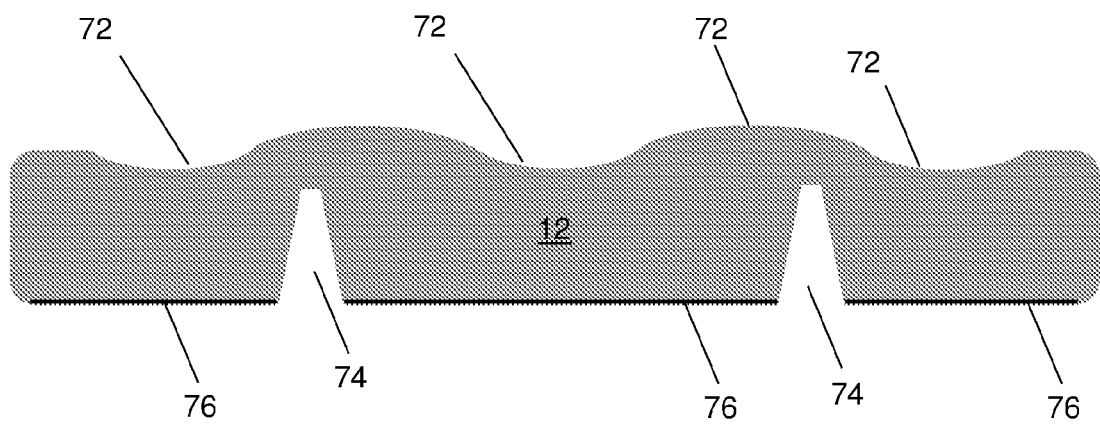
FIG. 9 is a side view of an alternative embodiment of the flexible light emitting pad having surface texturing and articulation structures.

The light emitting pad 12 may also include articulation structures 74 configured to allow the flexible light emitting pad 12 to more easily wrap around an infant. As shown in FIG. 9, the articulation structures 74 may comprise reliefs (e.g., voids) in the flexible light emitting pad 12. However, as will be understood by one of ordinary skill in the art, the articulation structures 74 may comprise any suitable structure for allowing the flexible light emitting pad 12 to more easily wrap around an infant.

As described above, the flexible light emitting pad 12 may be formed from molded silicone or urethane. Hydrogels may be added to the flexible light emitting pad 12 to improve oxygen permeability at the light emitting surface.

The surface texturing 72 may also include microlensing or similar surface treatment to target a specific light output distribution (e.g., maximizing uniformity or targeting particular areas on the infant, etc.). Alternatively or additionally, a diffuser sheet or a 2-D lensing sheet may be (1) placed on an emission surface 62 of the flexible light emitting pad 12 (i.e., the surface of the flexible light emitting pad adjacent the infant when placed on the flexible light emitting pad) or (2) embedded in the flexible light emitting pad 12 between the light source 14 and the emission surface 62 of the flexible light emitting pad 12.

The flexible light emitting pad 12 may also include a reflector 76 (also referred to as a reflective surface) positioned adjacent a back surface 64 of the flexible light emitting pad 12, such that the reflector 76 directs light emitted from the back surface 64 towards the light emitting surface 62. For example, the reflector 76 reflects light emitted by the light sources 14 that is propagating away from an infant located near a front surface of the flexible light emitting pad 12 back towards the infant.

Figure 10:
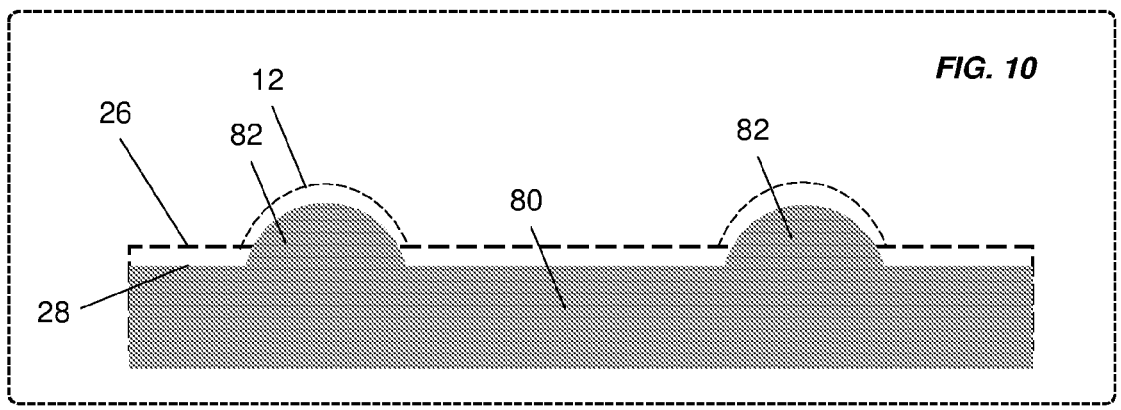
FIG. 10 is a side view of a schematic diagram of a base and the flexible light emitting pad of FIG. 1.

Turning to FIG. 10, instead of a garment 20, the flexible light emitting pad 12 may be positioned relative to the infant using a base 80. The base 80 may include positioning structures 82 to maintain a position of an infant on the base 80. For example, the flexible light emitting pad 12 may be laid on top of the base 80 and a premature infant may be laid on top of the light emitting pad 12. The positioning structures 82 may prevent the infant from rolling off of the base 80. As described above, the base 80 may be used to apply phototherapy to a back surface of the infant.

Figure 11:
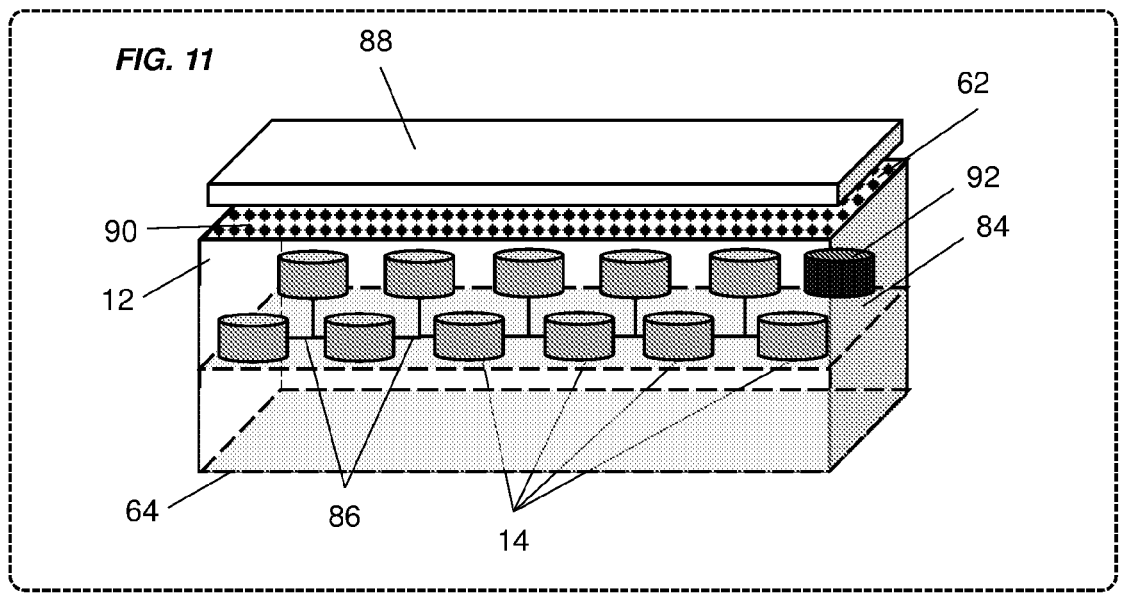
FIG. 11 is a perspective view of a schematic diagram of a phototherapy device including surface texturing, padding, and a sensor.

In the embodiment shown in FIG. 11, the support material 13 is a cloth material 84 and the light sources 14 and electrical connections 86 to the light sources 14 (e.g., for supplying power to the light sources 14) are printed onto the cloth material 84. In one embodiment, the cloth material 84, light sources, and electrical connections are incased in a gel. In another embodiment, the cloth material 84 may be a portion of the garment 20, such that the light sources 14 and the electrical connections 86 are printed onto the garment 20. For example, the light sources 14 and associated circuitry may be printed onto the cloth material 84 and a padding 86 may be placed over the cloth material 84. In this way, the padding 86 is positioned, such that the light emitting surface 62 is located between the light sources 14 and the padding 88 (i.e., so that the padding 86 is located between the infant and the light sources 14). The padding 88 may be configured (e.g., by using particular materials or by processing the materials in a particular manner) such that the padding 88 has little impact on light emitted by the light sources 14. For example, the padding 88 may reduce the optical power of the light emitted from the light sources by less than 5% or by less than 10%.

In one embodiment, the flexible light emitting pad 12 includes surface texturing 90 on the light emitting surface 62. The surface texturing 90 is configured to direct light emitted by the light emitting surface 62, such that the light emitted by the light emitting surface 62 has a specific light output distribution. For example, the surface texturing 90 may cause the light emitted from the light emitting surface 62 to have a more uniform distribution.

With continued reference to FIG. 11, the phototherapy device 10 may include a sensor 92 configured to sense at least one of biometric data of the infant or a property of the light emitted by the light sources 14. The circuitry 18 may receive an output of the sensor 92 and control the properties of light emitted by the light sources 14 based on the output of the sensor 92. For example, the circuitry 18 may measure a bilirubin level based on the output of the sensor 92.

In another example, the sensor 92 senses at least one an amount of light (e.g., optical power or applied irradiance) received by the infant or a temperature of the infant. In this example, the circuitry may reduce an output power of the light sources 14 when the sensed amount of light exceeds a dosage threshold or when the temperature exceeds a temperature threshold. Alternatively or additionally, the circuitry 18 may increase the output power of the light sources 14 (1) when the sensed amount of light is below the dosage threshold and (2) when the temperature is below the temperature threshold. The circuitry 18 may be configured to communicate with an electronic device. For example, the circuitry 18 may communicate wirelessly with an electronic device via Bluetooth or WIFI. Using the electronic device, a user may specify a dosage threshold (e.g., an applied irradiance) and/or temperature threshold.

In another embodiment, the sensor 92 senses a temperature of the infant and the electromagnetic radiation emitted by the light sources 14 includes infrared light. The circuitry may be configured to increase an output of infrared light by the light sources 14 when the sensed temperature of the infant is below a temperature threshold. Alternatively, the phototherapy device 10 may include heating elements (e.g., resistive heating elements) and the circuitry may cause these heating elements to generate heat when the sensed temperature of the infant is below a temperature threshold.

The sensor 92 may be one or more sensors for measuring light output by the light sources 14 (e.g., to determine dose received by the infant and/or to correct exposure time) and for measuring biometric data (e.g., heart rate, bilirubin count, temperature, etc.).

A frequent problem with phototherapy in cost-sensitive environments, particularly when delivered in the home, is the ability for an equipment supplier (typically a DME) to recover equipment after use. In one embodiment, the circuitry includes a tracking sensor and a communication interface. The tracking sensor identifies a location of the phototherapy device 10 and the communication interface sends the location identified by the tracking sensor. The tracking sensor may be a GPS sensor or any suitable sensor for identifying a location (e.g., relative location) of the phototherapy device 10. The communication interface may be a network interface such as a wireless network adaptor, an Ethernet network card, or any suitable device that provides an interface to a network for transferring data.

Figure 12:
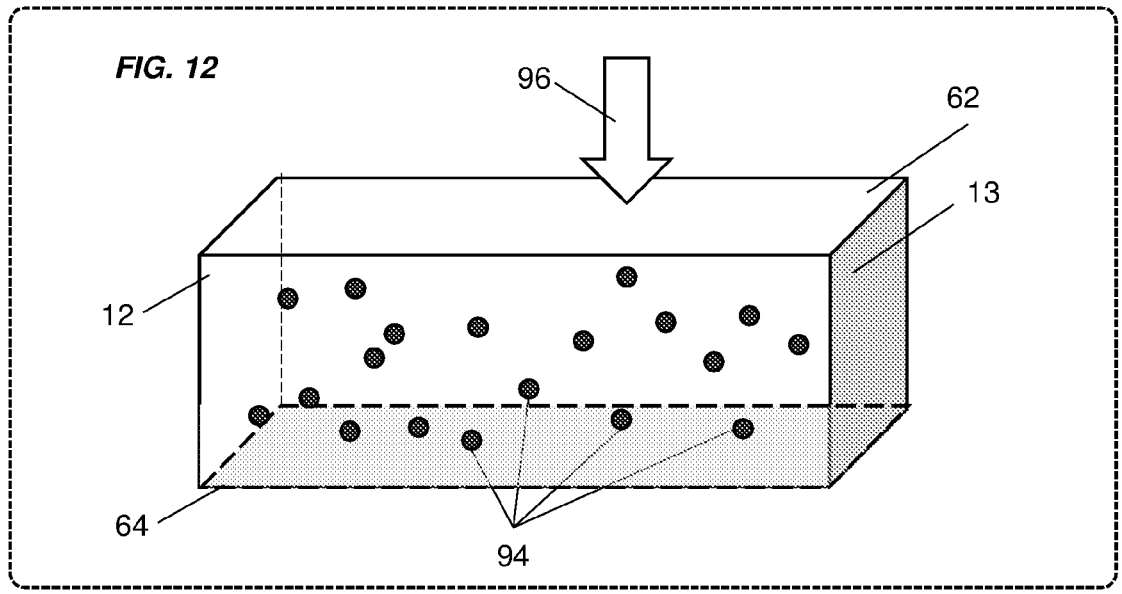
FIG. 12 is a perspective view of a flexible light emitting pad including wavelength converting nanoparticles sources.

In the embodiment shown in FIG. 12, the phototherapy device 10 includes the flexible light emitting pad 12 made of a flexible support material 13. The flexible light emitting pad 12 includes wavelength converting nanoparticles sources 94 configured to alter a wavelength of incident light 96. For example, the flexible support material 13 may be a sheet including quantum dots (QDs) as the wavelength converting nanoparticles sources 94. The flexible support material 13 may be a polymer sheet and the wavelength converting nanoparticles sources 94 may be dispersed throughout the polymer sheet. The flexible support material 13 may be cut into various shapes and inserted into the garment 20 described above. As will be understood by one of ordinary skill in the art, the flexible support material 13 is not limited to being made of a polymer, but may be composed of any material suitable for housing the wavelength converting nanoparticles sources 94.

The wavelength converting nanoparticles sources 94 of the flexible light emitting pad 12 may be configured to convert incident light (e.g., either solar light or white light) into treatment light having wavelengths with higher efficacy for phototherapy than the wavelengths of light included in the incident light. For example, sunlight contains a wide distribution of undesired and ineffective wavelengths including ultraviolet and infrared. The wavelength converting nanoparticles sources 94 may be used to boost the efficiency of solar treatment by converting the wavelength of incident light 96 into wavelengths of light that are more efficacious at treating jaundice.

The wavelength converting nanoparticles sources 94 may include upconverting nanoparticles and downconverting nanoparticles. The upconverting nanoparticles decrease a wavelength of the incident light 96 having a wavelength within an upconverting wavelength range. The downconverting nanoparticles increase a wavelength of the incident light 96 having a wavelength within a downconverting wavelength range. For example, the downconverters may be used to capture UV light and re-emit the light as effective blue light. Similarly, upconverters can be used to capture visible and IR light and re-emit as effective blue light. In this way, incident solar light or light from a typical white lamp may be converted with high efficiency to wavelengths of light used to treat jaundice (e.g., blue wavelengths) or other conditions treated with phototherapy.

In this embodiment, the flexible light emitting pad 12 may absorb and convert all wavelengths of incident light to wavelengths used in phototherapy. Alternatively, the flexible light emitting pad 12 could also contain a surface treatment configured to reflect unusable wavelengths (e.g., protecting an infant from sunburn and/or hyperthermia).

In this embodiment, the source of incident light may be external from the flexible light emitting pad 12. For example, the source of incident light may be the sun (i.e., solar light) or architectural lighting (e.g., overhead lamps). In this way, the flexible light emitting pad 12 in this embodiment may not require any power or electronics and could be easily stored/transported.

Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A phototherapy device for delivering light to an infant, the device comprising:
 a flexible light emitting pad made of a flexible support material and including light sources physically connected to the flexible support material and configured to emit electromagnetic radiation;

wherein the flexible light emitting pad includes a light emitting surface and a back surface opposite the light emitting surface; and wherein the light emitting surface includes surface texturing including depressions and protrusions located opposite the protrusions, such that the depressions act as channels for improving air flow to a skin of the infant.

2. The phototherapy device of claim 1, wherein the flexible support material is a gel and the light sources are encased in the gel.

3. The phototherapy device of claim 1, wherein:
the flexible light emitting pad additionally includes a light guide; and
the light emitted by the light sources is received, propagated, and emitted by the light guide.

4. The phototherapy device of claim 1, wherein the flexible light emitting pad includes articulation structures configured to allow the flexible light emitting pad to be wrapped around the infant.

5. The phototherapy device of claim 4, wherein the articulation structures comprise reliefs in the flexible light emitting pad.

6. The phototherapy device of claim 1, wherein the flexible support material is a cloth material and the light sources and electrical connections to the light sources are printed onto the cloth material.

7. The phototherapy device of claim 6, wherein the cloth material, light sources, and electrical connections are incased in a gel.

8. The phototherapy device of claim 6, wherein the cloth material comprises a portion of a garment, such that the light sources and the electrical connects are printed onto the garment.

9. The phototherapy device of claim 1, wherein the flexible light emitting pad includes at least one of:
a padding positioned such that:
the light emitting surface is located between the light sources and the padding; or
surface texturing, wherein:
the surface texturing is included in the light emitting surface; and
the surface texturing is configured to direct light emitted by the light emitting surface such that the light emitted by the light emitting surface has a specific light output distribution.

10. The phototherapy device of claim 1, further comprising a garment configured to:
receive the infant and the flexible light emitting pad; and
maintain the position of the flexible light emitting pad relative to the infant.

11. The phototherapy device of claim 10, wherein:
the garment includes an inner surface configured to be located adjacent the infant when the infant and the flexible light emitting pad are positioned within the garment and an outer surface opposite the front surface; and
the outer surface is opaque to light emitted by the light sources and/or includes a reflector configured to reflect light emitted by the light sources towards the inner surface.

12. The phototherapy device of claim 10, wherein the garment includes a receiving location configured to receive the flexible light emitting pad and to maintain a position of the flexible light emitting pad relative to the infant.

13. The phototherapy device of claim 12, wherein the receiving location is a pocket and the pocket includes:
an outer wall and an inner wall located opposite the outer wall;
the inner wall is positioned between the infant and the flexible light emitting pad when the flexible light emitting pad is received by the pocket and the infant is received by the garment; and
the inner wall is at least partially transparent to light emitted by the light sources.

14. The phototherapy device of claim 10, wherein the garment comprises a sack comprising:
a closed bottom edge;
a partially closed top including a hole through which a neck of the infant extends when the infant is received in the garment; and
two partially closed sides including arm holes through which arms of the infant extend when the infant is received in the garment.

15. The phototherapy device of claim 10, wherein:
the garment comprises a wrap configured to be wrapped around and swaddle the infant, such that movement of arms of the infant is restricted;
the wrap includes a top surface located opposite a bottom surface;
the bottom surface of the wrap faces towards the infant when the infant is received in the garment and when the infant is swaddled by the wrap;
the bottom surface has a first fastener; and
the top surface has a second fastener configured to releasably engage with the first fastener.

16. The phototherapy device of claim 10, wherein, when both the infant and the flexible light emitting pad are received by the garment, light emitted by the light sources illuminates a torso of the infant.

17. The phototherapy device of claim 1 further comprising:
a sensor configured to sense at least one of biometric data of the infant or a property of the light emitted by the light sources; and
circuitry configured to control properties of light emitted by the light sources to modulate an amount of light delivered to the infant via the light sources to provide a therapeutically effective dose, by:
receiving an output of the sensor and controlling the properties of light emitted by the light sources based on the output of the sensor.

18. The phototherapy device of claim 17, wherein the circuitry is configured to modulate the amount of light to provide a therapeutically effective dose to treat jaundice in the infant.

19. The phototherapy device of claim 17, wherein the circuitry is configured to measure a bilirubin level based on the output of the sensor.

20. The phototherapy device of claim 17, wherein:
the sensor is configured to sense an amount of light received by the infant; and
the circuitry is configured to at least one of:
reduce an output power of the light sources when the sensed amount of light exceeds a dosage threshold; or
increase the output power of the light sources when the sensed amount of light is below the dosage threshold.

21. The phototherapy device of claim 17, wherein:
the sensor is configured to sense a temperature of the infant;

the electromagnetic radiation emitted by the light sources includes infrared light; and the circuitry is configured to increase an output of infrared light by the light sources when the sensed temperature of the infant is below a temperature threshold.

22. The phototherapy device of claim 17, further comprising a reflective surface, wherein:

the flexible light emitting pad includes a light emitting surface and a back surface opposite the light emitting surface; and the reflective surface is positioned adjacent to the back surface, such that the reflective surface directs light emitted from the back surface towards the light emitting surface.

23. The phototherapy device of claim 17, wherein the flexible light emitting pad and/or the garment comprises a breathable material having a moisture vapor transmission rate ("MVTR") of at least 500 g/m$^2$/24 hrs.

* * * * *